United States Patent
Bates

(10) Patent No.: US 7,648,495 B2
(45) Date of Patent: Jan. 19, 2010

(54) APPARATUS FOR THE DELIVERY OF DRUGS OR GENE THERAPY INTO A PATIENT'S VASCULATURE AND METHODS OF USE

(75) Inventor: Mark C. Bates, Charleston, WV (US)

(73) Assignee: Nexeon MedSystems, Inc., Charleston, WV (US)

(*) Notice: Subject to any disclaimer, the term of this patent is extended or adjusted under 35 U.S.C. 154(b) by 621 days.

(21) Appl. No.: 10/822,037

(22) Filed: Apr. 8, 2004

(65) Prior Publication Data
US 2004/0193137 A1 Sep. 30, 2004

Related U.S. Application Data

(62) Division of application No. 09/648,257, filed on Aug. 25, 2000, now Pat. No. 6,740,331.

(51) Int. Cl.
*A61K 9/22* (2006.01)
(52) U.S. Cl. ............ 604/890.1; 604/891.1; 604/93.01; 604/104
(58) Field of Classification Search ............ 604/890.1, 604/892.1, 93.01, 104–109
See application file for complete search history.

(56) References Cited

U.S. PATENT DOCUMENTS

| | | | |
|---|---|---|---|
| 4,619,246 A | 10/1986 | Molgaard-Nielsen et al. | |
| 5,180,368 A | 1/1993 | Garrison | |
| 5,328,470 A | 7/1994 | Nabel et al. | |
| 5,603,694 A | 2/1997 | Brown et al. | |
| 5,713,863 A | 2/1998 | Vigil et al. | |
| 5,800,507 A | 9/1998 | Schwartz | |
| 5,911,704 A * | 6/1999 | Humes | 604/93.01 |
| 6,245,012 B1 * | 6/2001 | Kleshinski | 623/1.11 |
| 6,280,414 B1 | 8/2001 | Shah et al. | |
| 6,740,331 B1 | 5/2004 | Bates et al. | |
| 2001/0001817 A1 | 5/2001 | Humes | |

(Continued)

FOREIGN PATENT DOCUMENTS

FR 2 764 503 A1 12/1998

(Continued)

OTHER PUBLICATIONS

USPTO Non-Final Office Action for U.S. Appl. No. 09/648,257, 8 pages (mailed Nov. 6, 2002).

(Continued)

*Primary Examiner*—Nicholas D Lucchesi
*Assistant Examiner*—Laura A Bouchelle
(74) *Attorney, Agent, or Firm*—Jones Day; Nicola A. Pisano; Jaime D. Choi

(57) ABSTRACT

Methods and apparatus are provided for delivering drugs or gene therapy within a patient's vessel. In a preferred embodiment, the apparatus comprises a material eluting a bioactive substance held in place within the patient's vessel by an anchor. The anchor and eluting material are sized and/or collapsible from a delivery configuration, in which the anchor and material may be delivered into the patient's vasculature within a delivery sheath, to a deployed configuration, wherein the anchor engages an interior wall of the patient's vessel. The eluting material may elute recombinant genes, drugs, or any other bioactive substance.

17 Claims, 7 Drawing Sheets

U.S. PATENT DOCUMENTS

| | | |
|---|---|---|
| 2002/0090388 A1 | 7/2002 | Humes et al. |
| 2005/0064009 A1 | 3/2005 | Bates |

FOREIGN PATENT DOCUMENTS

| | | |
|---|---|---|
| WO | WO 9526168 A1 * | 10/1995 |
| WO | WO 96/39098 | 12/1996 |
| WO | WO 96/39098 A | 12/1996 |

OTHER PUBLICATIONS

USPTO Notice of Allowance for U.S. Appl. No. 09/648,257, 8 pages (mailed Jan. 9, 2004).

USPTO Non-Final Office Action for U.S. Appl. No. 10/864,936, 5 pages (mailed Jan. 6, 2009).

USPTO Non-Final Office Action for U.S. Appl. No. 10/864,936, 8 pages (mailed Jul. 25, 2008).

* cited by examiner

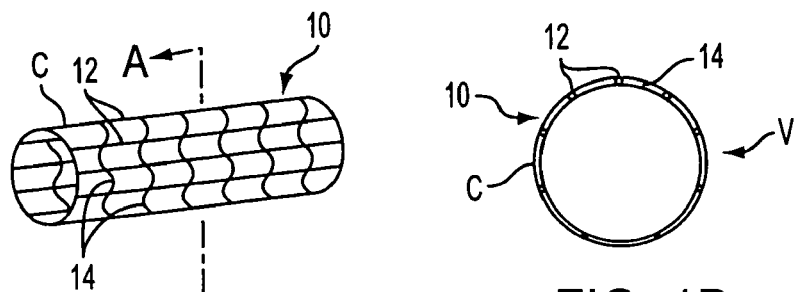
FIG. 1A (PRIOR ART)
FIG. 1B (PRIOR ART)
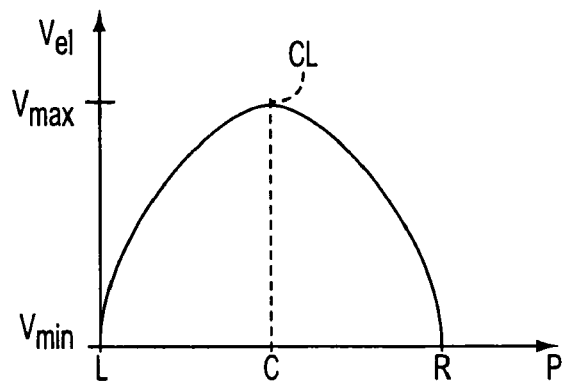
FIG. 2
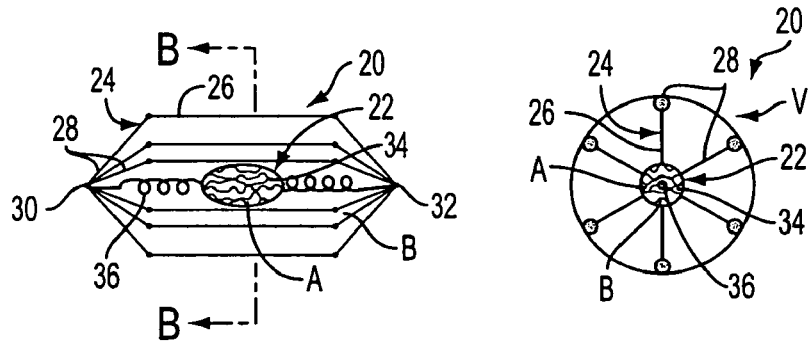
FIG. 3A
FIG. 3B
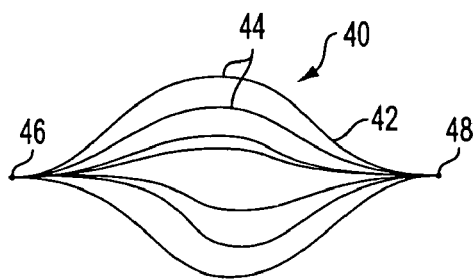
FIG. 4

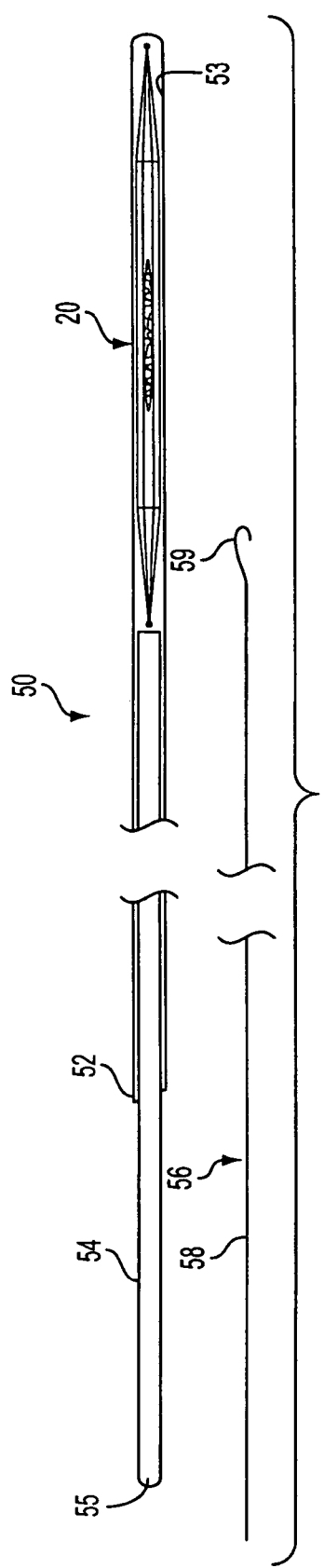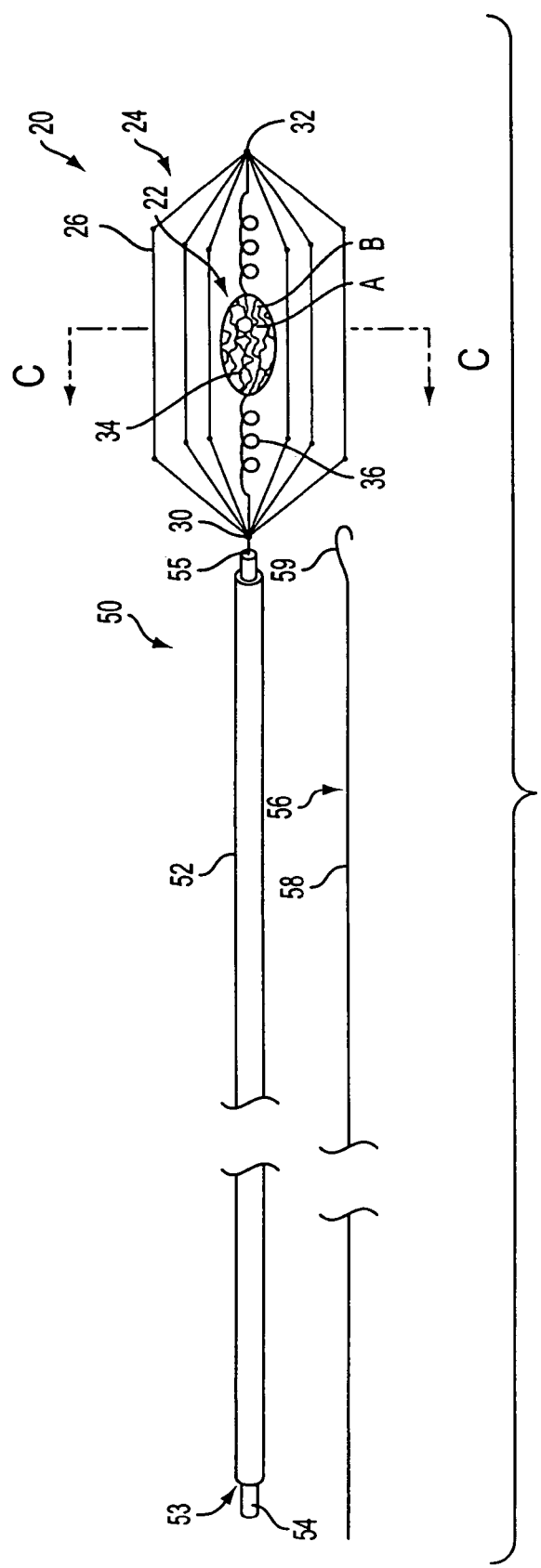
FIG. 5A
FIG. 5B

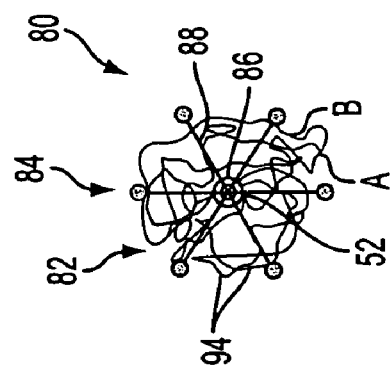
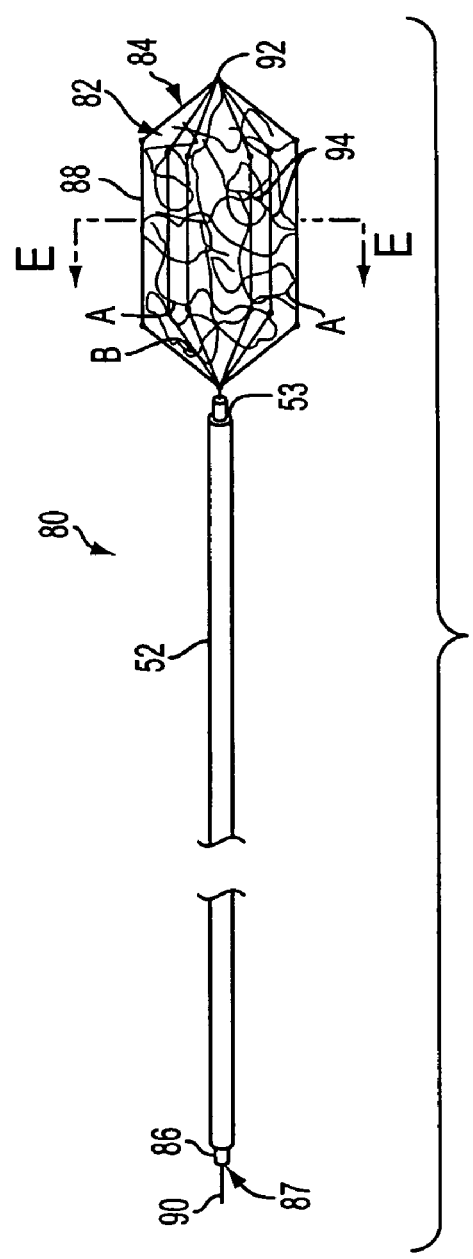
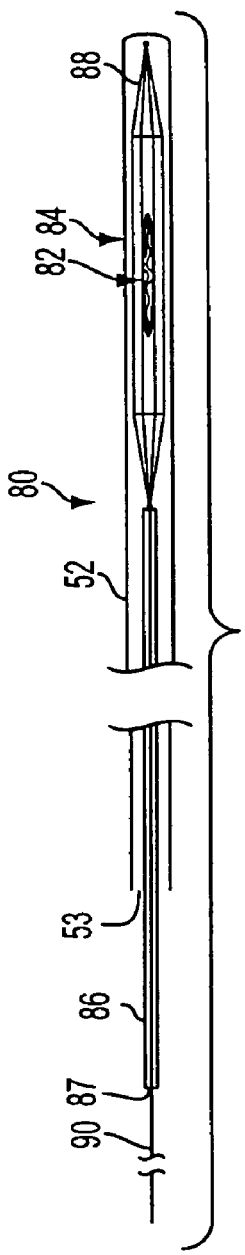
FIG. 7B
FIG. 7A
FIG. 7C

APPARATUS FOR THE DELIVERY OF DRUGS OR GENE THERAPY INTO A PATIENT'S VASCULATURE AND METHODS OF USE

FIELD OF THE INVENTION

This invention relates to drug delivery and gene therapy. More particularly, the present invention provides methods and apparatus for the delivery of drugs or gene therapy, or both, into a patient's vasculature.

BACKGROUND OF THE INVENTION

According to the National Cancer Institute, approximately 4,000 specific conditions are known to be caused by genetic detects. The GeneMed Network states that each human being carries roughly a half dozen defective genes, and that about one in ten people has or will develop an inherited genetic disorder.

A composite of approximately 150,000 individual genes constitutes a human being. Variation in the structure of these genes can lead to disease. Many diseases are hereditively passed by a single gene, while many others are influenced by a collection of genes.

Several years ago, the Human Genome Project began mapping every human gene. The project is fostering an understanding of the very foundation of human disease and is enabling new therapies to treat and predict the onset of disease. One such therapy is gene therapy, which seeks to directly and beneficially modify the expression of genes through delivery of engineered genetic material. Foreign nucleotide sequences of either DNA or RNA are inserted into a patient's cells to result in either expression of non-integrated sequences or integration of sequences directly into the DNA of the cells.

Safe and efficient delivery of nucleotide sequences to appropriate cells poses one of the primary challenges to gene therapy. Vectors, which encapsulate therapeutic genes, have been developed to deliver the sequences. These vectors may be either viral or synthetic. Viral vectors, derived from viruses, are the primary vectors in experimental use today. Viruses efficiently target cells and deliver genome, which normally leads to disease. However, viral vectors for gene therapy are modified so that they may not cause disease. Rather, therapeutic recombinant genes are inserted into the vectors and delivered to target cells. Optimally, the modified viruses retain their ability to efficiently deliver genetic material while being unable to replicate.

Research in the field of gene therapy is still in the formative stages. Human trials only began in 1990 with ex vivo techniques, wherein a patient's cells were harvested and cultivated in a laboratory and incubated with vectors to modify their genes. Cells were then harvested and intramuscularly transplanted back into the patient. Trials quickly shifted to in vivo techniques, in which viral vectors are administered directly to patients, again intramuscularly. A variety of diseases are currently being evaluated as candidates for gene therapy, and a need exists in the art for improved vector delivery techniques.

While significant progress has been made, current gene therapy delivery techniques have many drawbacks. Viral vectors are inherently dangerous due to the innate ability of viruses to transmit disease. Furthermore, long-term effects of using viruses as delivery vehicles are unclear. Chances for error in modifying the viruses to vectors are significant, and consequences may be substantial, including potential irreversible alteration of the human gene pool. Also, delivery of the vectors to an efficacious portion of diseased cells has proven difficult and expensive.

Synthetic vectors have been developed to address the potential for disease transmission with viral vectors. These vectors are complexes of DNA, proteins, or lipids, formed in particles capable of efficiently transferring genes. However, synthetic vectors have thus far proved less effective than viral vectors and have been slower to gain acceptance.

Perhaps even more problematic than limitations of the vectors, intramuscular in vivo techniques, wherein vectors are delivered into a patient's muscle tissue, have proven somewhat ineffective in clinical use. Systemic expression of inserted sequences is not realistic since therapy is localized.

In view of the drawbacks associated with previously known methods for delivery of gene therapy, it would be desirable to provide methods and apparatus that overcome such drawbacks.

It further would be desirable to provide methods and apparatus for delivery of gene therapy that mitigate the risk of disease transmission.

It still further would be desirable to provide methods and apparatus for providing localized delivery of genes or bioactive agents that are relatively inexpensive, as compared to current techniques.

It would be desirable to provide methods and apparatus for delivery of gene therapy that are suited for systemic delivery of viral vectors, synthetic vectors, drugs, or other therapeutic agents.

It would also be desirable to provide methods and apparatus that efficiently deliver genes to an efficacious portion of diseased cells.

SUMMARY OF THE INVENTION

In view of the foregoing, it is an object of the present invention to provide methods and apparatus for delivery of gene therapy that overcome drawbacks associated with previously known methods and apparatus.

It is also an object of the present invention to provide methods and apparatus that mitigate the risk of disease transmission.

It is another object to provide relatively inexpensive methods and apparatus for localized delivery of genes or bioactive agents.

It is an object to provide methods and apparatus for delivery of gene therapy that are suited for systemic delivery of viral vectors, synthetic vectors, drugs, or other therapeutic agents.

It is yet another object to provide methods and apparatus that efficiently deliver genes to an efficacious portion of diseased cells.

These and other objects of the present invention are accomplished by providing methods and apparatus for the delivery of gene therapy that expose one or more recombinant genes directly to a patient's bloodstream in a region of diseased tissue. A significant portion of blood that come into contact with the genes, which may or may not be encapsulated in vectors, is expected to incorporate the genes directly into its genome.

In a preferred embodiment, apparatus of the present invention comprises an eluting material held in place within a patient's vessel by an anchor. The anchor and eluting material are sized and/or expandable from a delivery configuration, in which the mechanism and material may be delivered into the patient's vasculature within a delivery sheath, to a deployed configuration, wherein the anchor engages an interior wall of the patient's vessel. The eluting material may elute recombinant genes, or, alternatively, it may elute drugs or other bioactive or therapeutic agents.

Methods of using the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 1A and 1B are views of a prior art eluting stent shown, respectively, in isometric view and in cross-section along view line A-A of FIG. 1A within a patient's vessel;

FIG. 2 is a graph illustrating velocity profile through a cross-section of a patient's vessel;

FIGS. 3A and 3B are views of apparatus constructed in accordance with the present invention shown, respectively, in side view in an expanded deployed configuration and in cross-section along view line B-B within a patient's vessel;

FIG. 4 is a side view of an alternative embodiment of the anchor of, the present invention in an expanded deployed configuration;

FIGS. 5A and 5B are views of delivery and retrieval apparatus of the present invention in use with the apparatus of FIGS. 3, shown, respectively, in side-sectional view in a collapsed delivery configuration and in side view in an expanded deployed configuration;

FIGS. 7A-7C are views of another alternative embodiment shown, respectively, in side view in an expanded deployed configuration, in cross-section along sectional view line D-D of FIG. 7A, and in side-sectional view in a collapsed delivery configuration;

DETAILED DESCRIPTION OF THE INVENTION

Figure 6B:
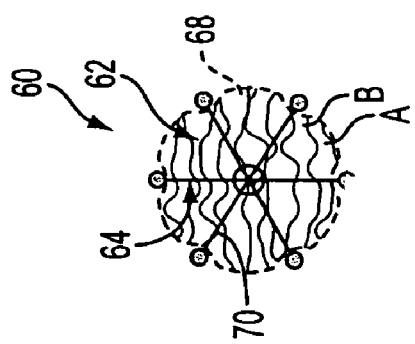
FIGS. 6A-6C are views of an alternative embodiment of the apparatus of FIGS. 5 shown, respectively, in side view in an expanded deployed configuration, in cross-section along sectional view line C-C of FIG. 6A, and in side-sectional view in a collapsed delivery configuration.

The present invention provides methods and apparatus for the delivery of drugs or gene therapy. Referring to FIG. 1, prior art apparatus for delivering a bioactive substance into a vessel is described. As seen in FIG. 1A, eluting stent 10 comprises linear members 12 and expandable radial members 14. Stent 10 is coated with coating C of a bioactive substance. Stent 10 is expanded within vessel V to engage an interior wall of the vessel, as seen in FIG. 1B. The bioactive substance of coating C is eluted into blood passing through vessel V.

FIG. 2 graphs the velocity profile of bloodflow through a cross-section of vessel V. Bloodflow velocity Vel is presented as a function of position P within vessel V. Positions at the left wall L, center C, and right wall R of vessel V are labeled along the ordinate axis. Likewise, minimum velocity Vmin and maximum velocity Vmax are labeled along the abscissa axis. Note that minimum velocity Vmin occurs at the vessel wall. Velocity increases at positions distant from vessel V, reaching the maximum Vmax at the center C of the vessel. Blood thus establishes a cylindrical, 3-dimensional Poiseulle flow, as illustrated by revolving the graph of FIG. 2 about center line CL.

Stent 10 of FIG. 1B abuts against the interior wall of vessel V, where bloodflow velocity Vel approaches its minimum Vmin. The stent therefore is ineffective in delivering the bioactive substance of coating C to the bloodstream, since stent 10 is only exposed to a small, near-stagnant portion of blood flowing through vessel V.

With reference now to FIGS. 3A and 3B, apparatus constructed in accordance with the principles of the present invention is described. Apparatus 20 is configured to deliver a bioactive substance to the bloodstream much more efficiently by exposing the substance to the bloodstream at areas distant from the vessel wall, where blood flows with higher velocity. Apparatus 20 comprises eluting material 22 disposed within anchor 24.

Anchor 24 comprises collapsible cage 26, which is adapted for semi-permanent implantation within a patient's vessel. Cage 26 is formed from a plurality of preformed segments 28. Segments 28 are joined together at their proximal ends at joint 30 and at their distal ends at joint 32.

Segments 28 preferably are fabricated from nickel-titanium wires, which may be welded at joints 30 and 32. Segments 28 may be substantially straight, or together may have a sinusoidal shape, as discussed hereinbelow with respect to FIG. 4. Cage 26 is able to resiliently expand from a delivery configuration, suited for transluminal insertion into a patient's vasculature, to the deployed configuration of FIG. 3A, wherein anchor 24 is adapted to engage an interior wall of the patient's vessel V, as seen in FIG. 3B.

Eluting material 22 comprises swellable pellet 34, which is attached to joints 30 and 32 by extensible band 36. Band 36 is further expected to facilitate expansion of cage 26. Extensible band 36 may, for example, comprise a spring. Pellet 34 is sized such that it may initially be transluminally delivered into the patient's vasculature. Upon exposure to blood flow within vessel V, pellet 34 swells so that it may contact a substantial portion of blood flowing at high velocity near the center of the vessel.

Pellet 34 comprises a bioactive substance B, which may include gene therapy sequences (encapsulated within vectors or alone) drugs, or any other bioactive or therapeutic agent. When delivered within the vasculature, blood flows through pellet 34 and comes into contact with bioactive substance B, thereby exposing the cells, as well as downstream capillary beds, to the substance and providing localized therapy.

Optionally, apparatus 20 may further comprise an anti-clotting agent A, such as heparin, coumadin, or aspirin, to prevent clotting around or within pellet 34 or cage 26. Alternatively, clotting may be preferred in order to kill unwanted or diseased downstream tissue. The central location of substance B within vessel V, as seen in FIG. 3B, contrasted with the location of coating C of stent 10 in FIG. 1B, illustrates a primary advantage of the present invention over previously known vascular elution techniques: bioactive substance B of apparatus 20 is exposed to bloodflow of relatively high velocity.

When used in drug delivery applications, substance B may, for example, comprise a therapeutic toxin, such as a chemotherapy drug. Drugs for chemotherapy are generally toxic to the entirety of an organism, not just cancer cells. Thus, delivery of these drugs directly into the vasculature, via sustained release in an arterial division supplying a tumor, is expected to provide more focused therapy. Substance B alternatively may comprise antibiotics. In patients with, for example, a compromised immune system or deep seeded infections, delivery of antibiotics directly into an abscess or infected area may be beneficial.

Furthermore, prolonged systemic delivery of any medication or gene therapy is expected through placement of apparatus 20 in a central vein of a patient's vasculature. Current techniques only provide sustained drug infusion through central intravenous ("IV") access, or through chronic, specifically-designed, IV devices. Conversely, apparatus 20 may be deployed in a central vein and then removed at a later time, for example, one to two weeks later. During that time period, apparatus 20 may provide systemic treatment to the patient, thereby eliminating the risk of infection from prolonged IV use.

Referring to FIG. 4, an alternative anchor in accordance with the present invention is described. Anchor 40 comprises sinusoidal cage 42, which is adapted for use with an eluting material such as material 22. Cage 42 is formed from a plurality of sinusoidal segments 44. Segments 44 are joined together at their proximal ends at joint 46 and at their distal ends at joint 48.

Segments 44 preferably are fabricated from nickel-titanium wires, which may be welded at joints 46 and 48. Like cage 26 of FIGS. 3, sinusoidal cage 42 is able to expand from a delivery configuration suited for transluminal insertion into a patient's vasculature, to the deployed configuration of FIG. 4, wherein anchor 40 is adapted to engage an interior wall of the patient's vessel. The sinusoidal shape of anchor 40 is expected to facilitate rapid and reliable deployment and retrieval.

Referring now to FIGS. 5, delivery and retrieval apparatus of the present invention are described. Apparatus 50 comprises delivery sheath 52, pusher 54, and retriever 56, as well as apparatus 20 of FIGS. 3A and 3B. In FIG. 5A, pusher 54 and apparatus 20 are coaxially disposed within lumen 53 of sheath 52. Cage 26 is not connected to pusher 54 and is adapted for semi-permanent implantation within a patient's vessel.

Cage 26 is expanded by distally advancing pusher 54 to push the cage out of lumen 53. Alternatively, sheath 52 may be proximally retracted while pusher 54, which abuts cage 26, is held stationary, thereby pushing the cage out of the sheath. Cage 26 then resiliently expands to the deployed configuration of FIG. 5B. Cage 26 and pellet 34 are implanted within the vessel for a predetermined period of time, after which the pellet may be removed from the patient's vasculature with retriever 56.

Retriever 56 comprises elongated member 58, which terminates at a distal end in hook 59. In order to retrieve apparatus 20, pusher 54 is removed from lumen 53 and replaced by retriever 56. Hook 59 may then be advanced beyond the distal end of sheath 52 and into the interior of cage 26, then retracted such that it engages the cage at joint 30. Continued retraction causes cage 26 to collapse back to the delivery configuration of FIG. 5A within sheath 52. Retriever 56 may alternatively be advanced through optional lumen 55 of pusher 54.

With reference to FIGS. 6, an alternative embodiment of apparatus of the present invention, suited for temporary implantation, is described. Apparatus 60 comprises eluting material 62, anchor 64, delivery sheath 52, and guide wire 66. Eluting material 62 comprises spongy material 68 disposed within anchor 64.

Figure 6A:
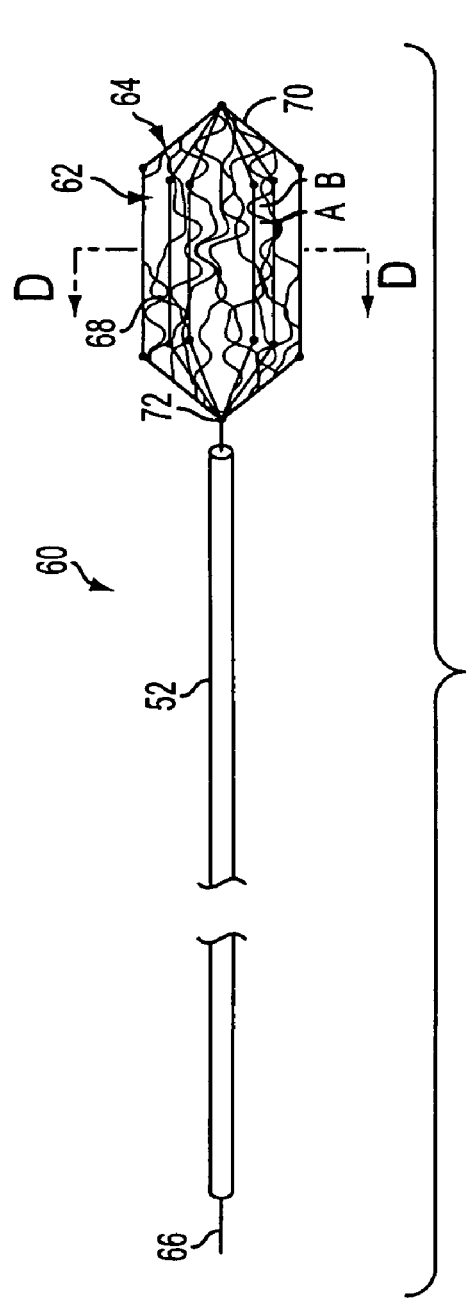
Figure 6C:
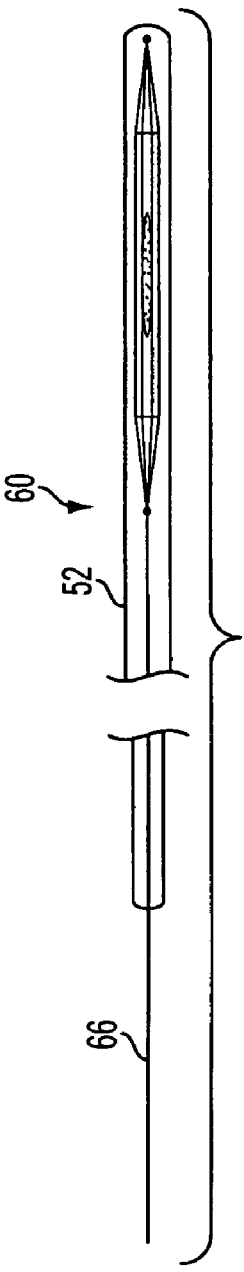

Anchor 64 comprises collapsible cage 70, which is identical to cage 26 described hereinabove, except that cage 70 is attached to guide wire 66 at proximal joint 72 to provide rapid retrieval of apparatus 60 after temporary implantation. Spongy material 20 and cage 70 collapse for delivery within sheath 52, as seen in FIG. 6C, and resiliently expand when delivered within the vasculature, as seen in FIGS. 6A and 6B. Spongy material 20 may, for example, be fabricated from an expandable and porous foam or a steel wool. Material 20 comprises bioactive substance B, as described hereinabove, and may optionally further comprise anti-clotting agent A, also described previously. As seen in FIG. 6E, material 20 covers a substantial portion of the patient's vessel in the expanded configuration, thereby exposing B to a substantial portion of blood passing therethrough.

Referring now to FIGS. 7A-7C, another alternative embodiment of apparatus in accordance with the present invention is described. Apparatus 80 comprises eluting material 82, anchor 84, and guide tube 86, as well as delivery sheath 52. Guide tube 86 is coaxially disposed within lumen 53 of sheath 52. Anchor 84 comprises collapsible cage 88, which is attached to guide tube 86. Cage 88 is similar to cage 70 of FIGS. 6, except that cage 88 connects to guide tube 86 in a manner that provides access to the interior of cage 88 through lumen 87 of tube 86.

Eluting material 82 comprises floppy elongated member 90, which passes through lumen 87 of tube 86 into the interior of cage 88, and is coupled at a distal end to joint 92 of cage 88. With cage 88 deployed in a patient's vessel, member 90 may be advanced while tube 86 is held stationary. Advancement causes member 90 to buckle, due to its attachment to joint 92 of cage 88. Continued advancement creates multiple turns 94 of material 82, which preferably occupy a substantial portion of the interior of cage 88, as seen in FIGS. 7A and 7B. Multiple turns 94 are coated with bioactive substance B, and may optionally be coated with anti-clotting agent A. Cage 88 also may be coated with agent A.

Apparatus 80 may be retrieved by proximally retracting elongated member 90 to remove turns 94 from the interior of cage 88. Cage 88 may then be collapsed within lumen 53 of delivery sheath 52 to facilitate delivery and retrieval from a patient, as seen in FIG. 7C.

Figure 8A:
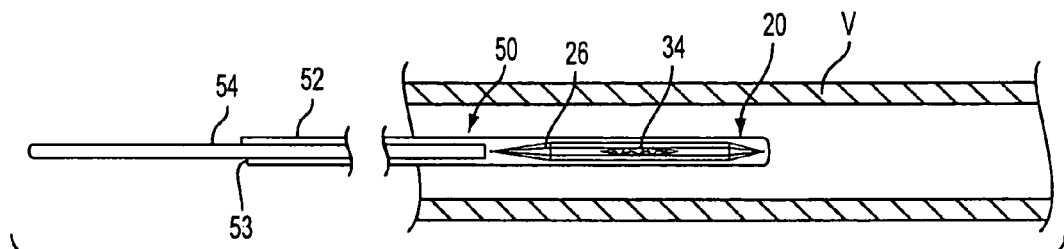
FIGS. 8A-8D are side-sectional views of the apparatus of FIG. 5 within a patient's vasculature demonstrating a method of use.

Referring now to FIGS. 8A-8D, a method of using the apparatus of FIG. 5 is described. As seen in FIG. 8A, with cage 26 and pellet 34 in the delivery configuration within delivery sheath 52, apparatus 20 is advanced into a patient's vessel V using, for example, well known percutaneous techniques. Cage 26 and pellet 34 are then expanded to the deployed configuration by distally advancing pusher 54 while delivery sheath 52 is held stationary, thereby advancing cage 26 out of lumen 53 and beyond a distal end of delivery sheath 52. Alternatively, pusher 54 may be held stationary while delivery sheath 52 is proximally retracted, again advancing cage 26 out of lumen 53.

Figure 8B:
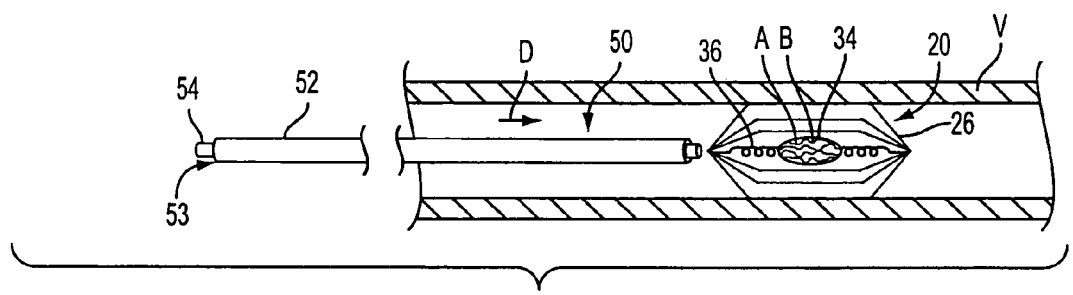

As seen in FIG. 8B, cage 26 resiliently expands to the deployed configuration, while water swellable pellet 34 expands upon contact with blood flowing through vessel V. The resiliency of joints 30 and 32, as well as the resiliency of extensible band 36, preferentially orient cage 26 in the deployed configuration, thereby establishing a lower energy state. Cage 26 engages an interior wall of vessel V and anchors pellet 34 in position within a region of high velocity bloodflow.

Blood flows through vessel V in direction D. As discussed previously, pellet 34 comprises bioactive substance B, which may include gene therapy sequences (either alone or encapsulated in a vector), drugs, or any other bioactive or therapeutic agent. It also optionally comprises an anti-clotting agent A, such as heparin, coumadin, or aspirin, to prevent clotting around or within apparatus 20. Alternatively, clotting may be preferred in order to kill unwanted or diseased downstream tissue.

Blood flows through pellet 34 and comes into contact with bioactive substance B, thereby exposing the cells, as well as downstream capillary beds, to the substance and providing localized therapy. When substance B comprises gene therapy vectors, as much as 30% of blood flowing past pellet 34 is expected to incorporate the vectors. Gene therapies suited for such localized delivery and expression include angiogenesis and revascularization. Delivery sheath 52 and pusher 54 may be removed from the patient, and apparatus 20 may be left in place within the patient for as much as 4 weeks.

Figure 8C:
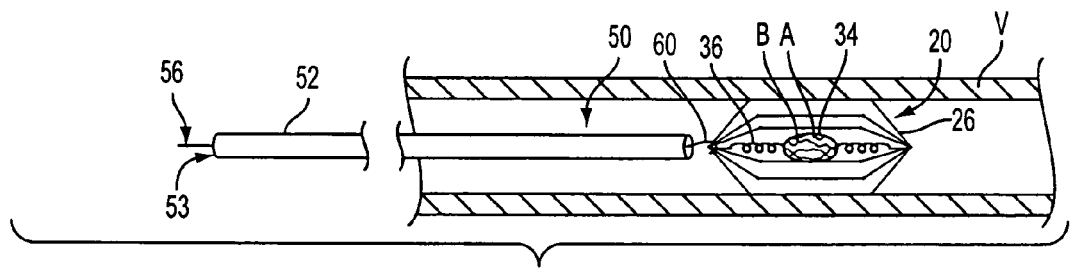
Figure 8D:
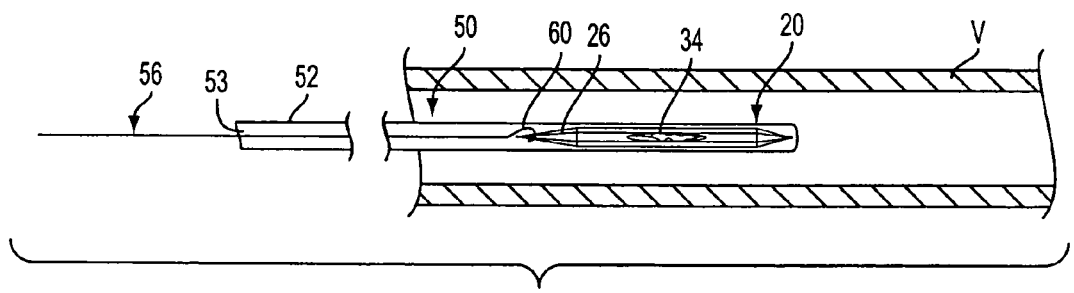

Upon completion of the procedure, sheath 52 is reintroduced into vessel V until it is disposed just proximal of cage 26. Retriever 56 is advanced through lumen 53 beyond the distal end of sheath 52 and into the interior of cage 26. Retriever 56 is then retracted proximally such that hook 60 engages joint 30 of cage 26, as seen in FIG. 8C. Continued retraction of retriever 56 collapses apparatus 20 back to the delivery configuration within sheath 52, as in FIG. 8D. Apparatus in accordance with the present invention may comprise one or more radiopaque features (not shown) to facilitate expansion or collapse of the anchor and eluting material. Apparatus 50 then is removed from vessel V.

Figure 9:
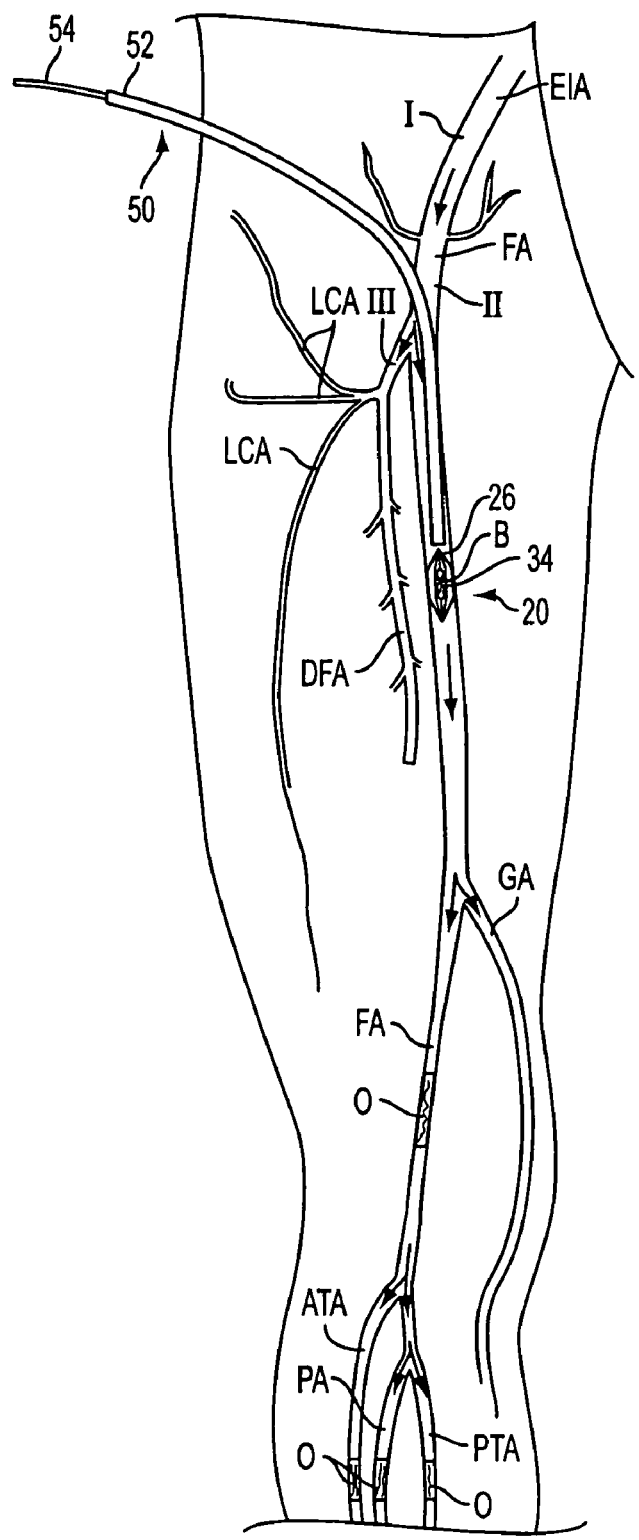
FIG. 9 is a side-sectional view of the apparatus of FIG. 5 within a patient's ischemic leg proximal of the patient's occluded superficial femoral artery, demonstrating a method of use in diffusing the occlusion.

With reference to FIG. 9, a method of using apparatus 50 in a drug delivery application to diffuse an occlusion in a patient's ischemic leg is described. FIG. 9 illustrates the primary arteries of the lower extremity, including the external iliac artery EIA, the femoral artery FA, the lateral circumflex femoral artery LCA, the deep femoral artery DFA, the genicular artery GA, the anterior tibial artery ATA, the peroneal artery PA, and the posterior tibial artery PTA. The femoral artery FA is shown occluded with occlusion O. The arteries distal of the femoral also may be occluded with occlusions O. If the occlusions are not diffused, the patient's leg below the occlusions will be unable to heal and may require amputation.

Apparatus 50 is shown percutaneously introduced into the patient's vasculature just proximal of a split between the femoral and the circumflex arteries. With cage 26 and pellet 34 disposed in the delivery state within sheath 52, apparatus 20 has been advanced distal of the split. Cage 26 and pellet 34 are shown expanded to the deployed configuration via relative movement between pusher 54 and delivery sheath 52, so that cage 26 engages the interior surface of fernoral artery FA.

Pellet 34 comprises bioactive substance B. In order to diffuse occlusions O, substance B preferably comprises a thrombolytic. Suitable thrombolytics include, for example, tissue plasminogen activator ("TPA"), streptokinase, and urokinase. Alternatively, bioactive substance B may comprise an anti-coagulant, for example, coumadin, heparin, aspirin, or GP IIb-IIIa inhibitors. In addition to diffusing occlusion O, anti-coagulants may be used to prevent clotting within and around cage 26 and pellet 34 during treatment. Bioactive substance B may still further comprise an antiplatelet medication. Anticoagulants, thrombolytics, and/or antiplatelet medications may also be used in conjunction with one another.

Bioactive substance B is carried downstream by blood flowing in a direction illustrated by arrows in FIG. 9. The agent diffuses occlusion O to restore proper blood flow to the patient's lower leg. Apparatus 20 then may be collapsed back to the delivery state within sheath 52, and apparatus 50 may be removed from the patient, as described hereinabove.

Depending on the shape, size, severity, or location of occlusions O, or depending on any of a variety of other factors, cage 26 alternatively may be deployed at or near locations marked I, II, and III in FIG. 9.

Figure 10:
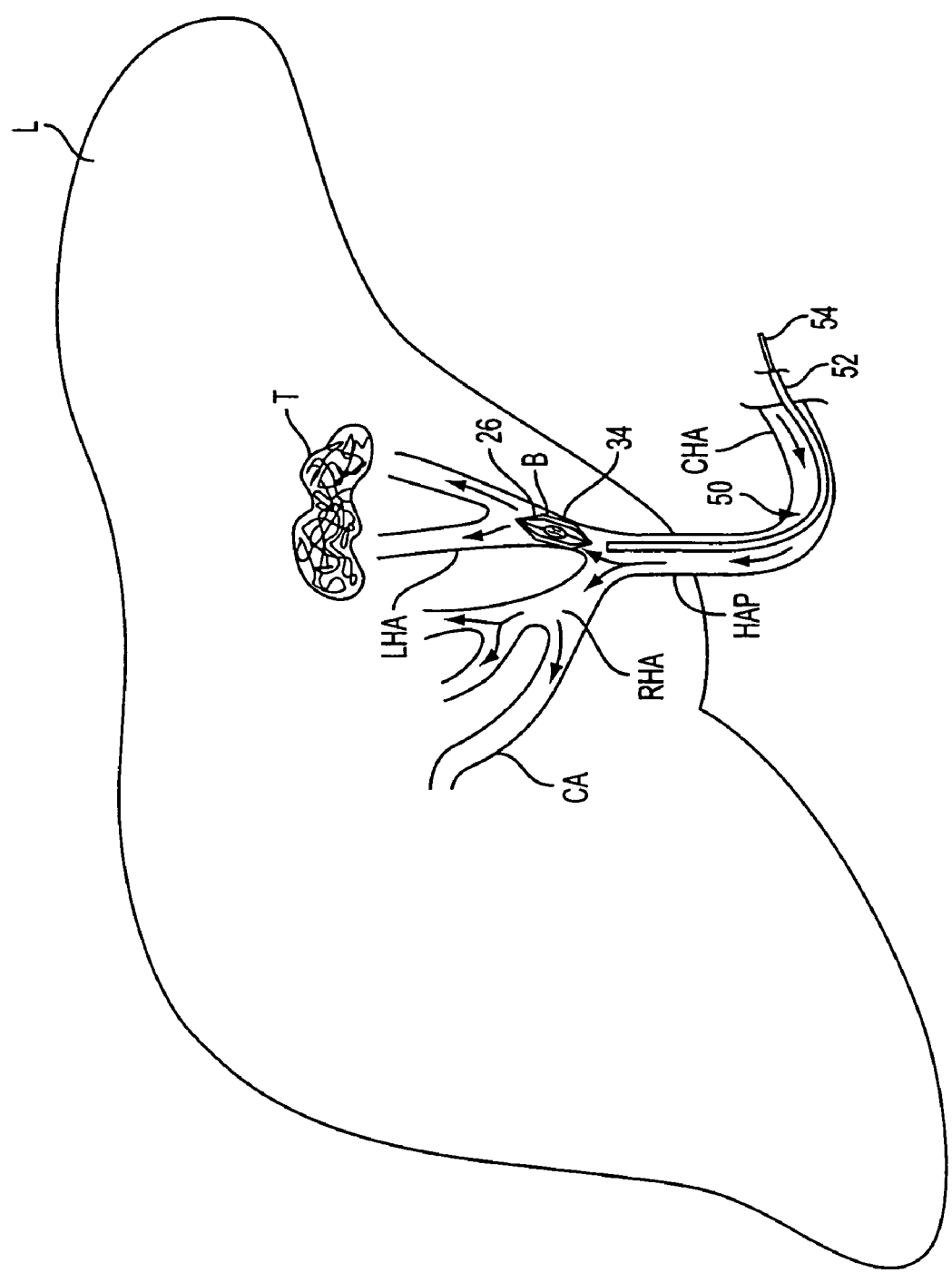
FIG. 10 is a side-sectional view of the apparatus of FIG. 5 within a patient's hepatic artery demonstrating a method of use in treating a tumor within the patient's liver.

Referring now to FIG. 10, a method of using apparatus 50 to treat tumorous tissue is described. FIG. 10 illustrates the primary arteries of a patient's liver L, including the common hepatic artery CHA, the hepatic artery proper HAP, the right hepatic artery RHA, the cystic artery CA (which feeds into the gallbladder), and the left hepatic artery LHA. Liver L includes tumorous tissue T just distal of left hepatic artery LHA, for which therapy is required.

Apparatus 50 has been percutaneously advanced and deployed within the left hepatic. Cage 26, with pellet 34 comprising bioactive substance B, engages an interior wall of left hepatic artery LHA. Blood flowing through the artery, in a direction illustrated by arrows in FIG. 10, passes through pellet 34, thereby contacting bioactive substance B on its path to tumorous tissue T. Bioactive substance B may comprise a gene therapy or a drug therapy, or both. With gene therapy, the agent seeks to kill the cancerous tissue by halting expression at the genomic level, for example, halting replication of new cancer cells. With drug therapy, the agent seeks to kill the tumorous tissue by poisoning it.

Although particular embodiments of the present invention have been described above in detail, it will be understood that this description is merely for purposes of illustration. Specific features of the invention are shown in some drawings and not in others; this is for convenience only, and any feature may be combined with another in accordance with the invention. Further variations will be apparent to one skilled in the art in light of this disclosure. For example, anchors in accordance with the present invention need not be expandable cages. Rather, they may comprise any of a variety of anchoring mechanisms suited for engaging a vessel wall. Likewise, a variety of alternative eluting materials and bioactive substances will be apparent to those of skill in the art. These and other variations are intended to fall within the scope of the appended claims.

What is claimed is:

1. A method of delivering a bioactive substance within a vessel, the method comprising:

providing apparatus comprising an anchor reversibly expandable from a delivery configuration to a deployed configuration, and an eluting material adapted to elute a bioactive substance, the eluting material comprising either a swellable pellet or a compressible foam having a compressed delivery state and an expanded state in situ;

expanding the anchor to the deployed configuration within the vessel, the anchor engaging an interior wall of the vessel;

permitting the eluting material to expand in volume within the anchor;

eluting the bioactive substance from the eluting material into blood flowing through the eluting material and through the anchor.

2. The method of claim 1 further comprising, prior to expanding the anchor:

disposing the anchor in the delivery configuration within a distal end of a lumen of a delivery sheath; and advancing the distal end of the delivery sheath to a delivery site within the vessel.

3. The method of claim 2, further comprising:

retracting the anchor within a distal end of the catheter.

4. The method of claim 2, further comprising, after expanding the anchor, removing the delivery sheath from the patient's vessel.

5. The method of claim 1, wherein eluting the bioactive substance comprises eluting a substance chosen from the group consisting of gene therapy vectors, gene therapy sequences, and drugs.

6. The method of claim 1, wherein providing apparatus comprising an anchor comprises providing a resiliently expandable cage.

7. The method of claim 1, further comprising:
after a predetermined period, advancing a catheter within the vessel and engaging the anchor;
collapsing the anchor to the delivery configuration; and
removing the apparatus from the patient's.

8. An intravascular device for delivering a bioactive substance into systemic circulation of an animal, the device comprising:
an anchor immobilizable to an inner wall of an intact blood vessel which, when immobilized in the blood vessel, permits blood in the vessel to pass therethrough; and
an eluting material adapted to elute the bioactive substance, which when introduced into the blood vessel is retained by the anchor and releases the bioactive substance into blood flowing therethrough, the eluting material comprising either a water-swellable pellet or a compressible foam.

9. The device of claim 8, wherein the anchor comprises at least one element biased in a radially outward direction when immobilized in the blood vessel.

10. The device of claim 8, wherein the anchor is a stent.

11. The device of claim 8, wherein the anchor comprises a head and a plurality of filaments attached by one end to the head.

12. The device of claim 11, wherein the anchor is an embolism anti-migration filter.

13. The device of claim 8, wherein the anchor comprises a receptacle for receiving the eluting material.

14. The device of claim 8, wherein the compressible foam is porous.

15. The device of claim 8, wherein the bioactive substance is a cardiovascular drug or a coagulation factor.

16. The device of claim 8, wherein the eluting material comprises a plurality of pre-selected drugs which are released into blood.

17. The device of claim 8, wherein the eluting material releases the bioactive substance over a pre-selected period of time.

* * * * *